US005198421A

United States Patent [19]

Chen et al.

[11] Patent Number: 5,198,421

[45] Date of Patent: Mar. 30, 1993

[54] PHOSPHORYLATED CYCLIC LIPOPEPTIDE

[75] Inventors: Shieh-Shung T. Chen, Morganville; David J. Mathre, Edison; Brian R. Petuch, Florence; Robert A. Reamer, Bloomfield, all of N.J.

[73] Assignee: Merck & Co., Inc., Rahway, N.J.

[21] Appl. No.: 691,606

[22] Filed: Apr. 26, 1991

[51] Int. Cl.[5] .......... A61K 37/02; C07K 7/54

[52] U.S. Cl. .......... 514/11; 514/9; 530/317; 530/323; 435/71.1; 435/71.3; 435/939; 930/270; 930/DIG. 536

[58] Field of Search .......... 530/317, 323; 514/9, 514/11; 435/71.3, 71.1, 939

[56] References Cited

U.S. PATENT DOCUMENTS

| | | | |
|---|---|---|---|
| 5,021,403 | 6/1991 | Sesin et al. | 514/9 |
| 5,049,546 | 9/1991 | Sesin et al. | 514/9 |

OTHER PUBLICATIONS

G. Pavanasasivam, et al., *Microbial Transformation of Macrocyclic Trichothecenes;* Appl. and Environ. Microbiol. Aug. 1983, pp. 480–483.

H. Holland, *Microbial hydroxylation of steroids. 7. Hydroxylation of β-nortestosterone and related compounds by Rhizopus arrhizus ATCC 11145, and 13C nuclear magnetic resonance spectra of some β-norsteroids;* Can.J.-Chem., vol. 59, 1981, pp. 1651–1655.

A. Clark et al., *Microbial Transformation of the Sesquiterpene Lactone Costunolide;* J.C.S. Perkin I, 1979, pp. 3022–3028.

C. Hufford, et al., *Metabolism of Imipramine by Microorganisms;* J. Pharm. Sci. vol. 70, No. 2, Feb. 1981, pp. 151–155.

H. Holland, et al., *Microbial hydroxylation of steriods;* Can. J. Chem., vol. 63, 1985, pp. 1127–1131.

L. Canonica, et al., *The Microbiological Oxidation of Insect Moulting Hormones,* J.C.S. Chem. Comm., 1974, pp. 656–657.

H. Holland, et al., *Microbial hydroxylation of steroids.5-.Metabolism of androst-5-ene-3,17-dione and related compounds by Rhizopus arrhizus* ATCC 11145, Can. J. Chem., vol. 57, 1979, pp. 436–440.

H. Holland, et al., *Microbial hydroxylation of steroids.6-.Hydroxylation of C-6-substituted androst-4-ene-3,17-diones by Rhizopus arrhizua ATCC 11145* Can. J. Chem., vol. 57, 1979, pp. 1585–1587.

*Primary Examiner*—Y. Christina Chan

*Attorney, Agent, or Firm*—Salvatore C. Mitri; Charles M. Caruso

[57] ABSTRACT

There is disclosed a monophosphorylated cyclic lipopeptide compound obtained by biophosphorylating a cyclic lipopeptide related to echinocandins and having a peptide skeleton bearing several hydroxy groups wherein in the phosphorylated cyclic lipopeptide, the phosphate group is attached to the hydroxy group of the 4-hydroxyproline component of the lipopeptide. The compounds are useful for the control of fungi and parasites.

6 Claims, 1 Drawing Sheet

PHOSPHORYLATED CYCLIC LIPOPEPTIDE

The present invention is directed to a selectively monophosphorylated cyclic lipopeptide compound obtained by biophosphorylating a cyclic lipopeptide related to echinocandins and having a peptide skeleton bearing several hydroxy groups wherein in said phosphorylated cyclic lipopeptide, the phosphate group is attached to the hydroxy group of the 4-hydroxyproline component of the lipopeptide.

Echinocandins or echinocandin compounds are cyclohexapeptide compounds having a lipophilic side chain and having antifungal properties. Many are natural products but many compounds are semi synthetic. The natural products are described in the literature as echinocandins, aculeacins, mulundocandin, by number designations or by structure. Many have been known a long time and the structure and properties may be found summarized in the CRC Handbook of Antibiotic Compounds, Vol IV, Part I, pp 355–367, CRC Press, Inc., Boca Raton, Fla. 1980. Still others include a more recently discovered compound such as that described in U.S. Pat. No. 4,931,352.

The present invention is especially directed to a compound having the formula (I) SEQ ID No: 1:

(I)

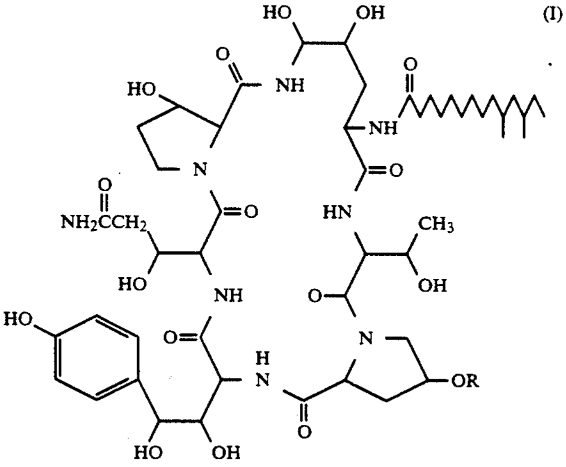

wherein R is

or a cation salt thereof

By "cation salt" is meant a salt of Li, K, Mg, Na, Ca, and ($C_1$–$C_4$ alkyl)ammonium.

When R is

the compound may be represented by formula (IA) (SEQ ID No: 1), and hereinafter referred to as Compound IA.

(IA)

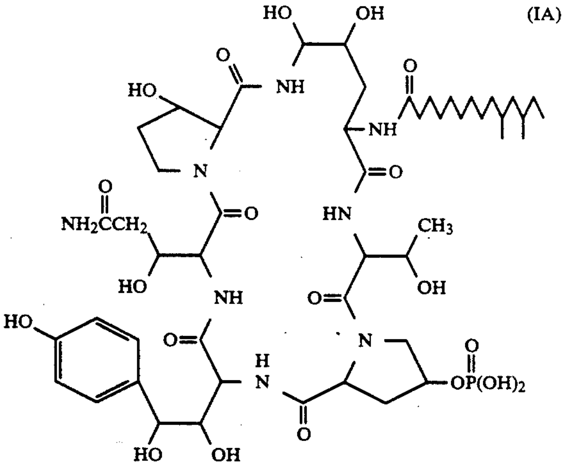

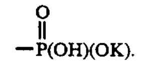

MASS SPECTRAL DATA

Figure 1:
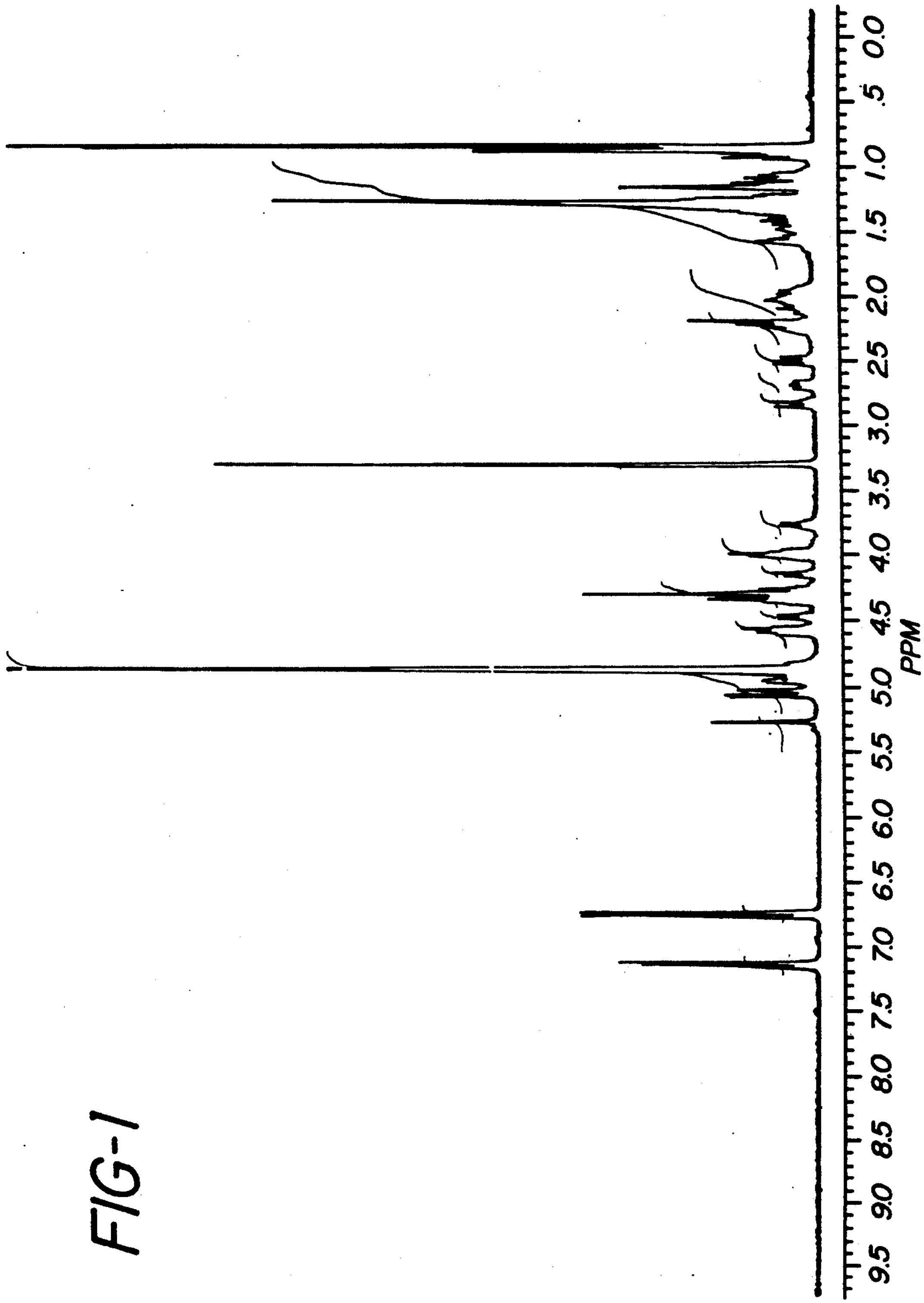
FIG. 1 is nuclear magnetic resonance spectrum of Compound I in which R is

Compound IA has a molecular weight of 1144 by FAB-MS (observed $(M+Na)^+$ of 1167).

NMR DATA $^1H$ NMR Spectra of the compound isolated as a monopotassium salt in $CD_3OD$ at 400 MHz is seen in FIG. 1; and $^{13}C$ NMR chemical shifts of the same isolate in $CD_3OD$ at 100 MHz are as follows: $\delta_c$ 177.2, 175.9, 174.3, 173.2, 172.9, 172.58, 172.57, 169.0, 158.4, 133.1, 129.6, 116.2, 77.0, 75.8, 75.2 (doublet, $J_{CP}$=4.0 Hertz), 74.3, 73.9, 70.6, 70.5, 69.7, 68.3, 62.7, 58.3, 56.3, 56.1, 55.6, 51.2, 47.0, 45.9, 39.4, 38.1, 37.6, 36.7, 35.0, 34.6, 32.9, 31.24, 31.20, 30.8, 30.6, 30.3, 28.1, 27.0, 20.7, 20.2, 19.8, 11.6.

On the basis of these and other data, Compound IA is believed with considerable certainty to have the structure indicated.

Compound IA is a white solid soluble in water and polar solvents such as lower alkanols and in dilute alkali metal, magnesium, calcium, and tetra (lower alkyl)ammonium bases. From the bases, salts in which R is a cation salt of phosphate may be obtained.

The compound of this invention has similar antibiotic properties as the non-phosphorylated compound and thus would be useful as an antibiotic for the control of parasites, especially *Pneumocystis carinii*, the causative agent of pneumocystis pneumonia, a particular problem with immune compromised patients, and for the control of fungi. Its antifungal properties are particularly useful against certain strains of yeast, such as *Candida albicans* and *Candida tropicalis.*

The compound in which R is

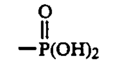

is conveniently produced by incubating a compound having the formula (Z) (Compound Z) SEQ ID No: 1

(Z)

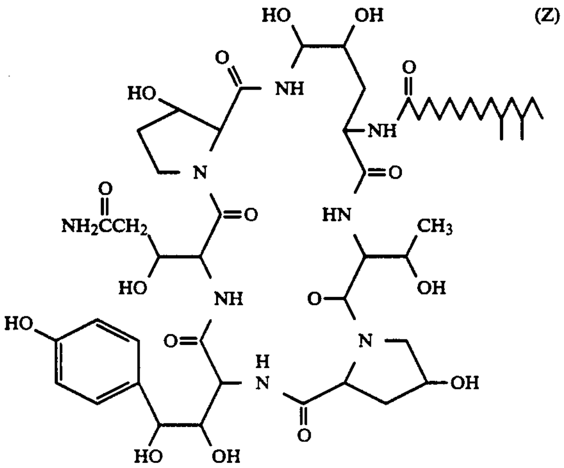

with induced resting cells of *Rhizopus arrhizus* ATCC 11145 maintained in the Merck Culture Collection as MF 4974. The culture was originally obtained from the American Type Culture Collection at 12301 Parklawn Drive, Rockville, Md. 20852.

Compound Z maybe produced by cultivating *Zalarion arboricola* ATCC 74030 in nutrient medium as hereinafter described as well as by methods described in copending applications Ser. No. 492,025, filed Mar. 12, 1990 now abandoned and Ser. No. 492,026, also filed Mar. 12, 1990 now U.S. Pat. No. 5,021,341 issued Jun. 4, 1991.

The microorganism *Rhizopus arrhizus* ATCC 11145 is also known as *Rhizopus oryzae* (J. J. Ellis, 1985, Mycologia 77: 243-247). The species has also been described under the names *Rhizopus nodosus* and *Rhizopus tritici*. The strain MF 4974, ATCC 11145, exhibits all the essential features of *R. arrhizus* described by M.A.A. Schipper under the name *R. oryzae*, CBS Studies in Mycology 25: 1-19 (1984). During a recent regrowth of MF4974 ATCC 11145, the following diagnostic characteristics were observed.

The strain is apparently heterothallic because zygospore spore formation was not observed. Colonies grow on most standard mycological media, but on cornmeal agar (Difco) are extremely fast-growing, reaching 35 mm in diameter in 36 hours at 20° C., reaching >90 mm in 36 hours at 37° C., with sporangiophores completely filling Petri dishes, hyaline at first but soon becoming pale yellowish gray to light gray, brownish gray, finally dark gray. Sporangiophores 200-1000 μm tall, 7.5-19 μm wide, aseptate, straight to curved at base, flared at apex, sometimes furcate, with walls slightly thickened, with minutely granular surface, pale yellowish brown or yellowish gray, arising from rhizoidal hyphae. Rhizoidal hyphae consisting of 3-10, thick, often contorted branches.

Sporangia globose to subglobose, slightly flattened on underside, 100-230 μm in diameter, opaque, with surface spiny, dark gray to black. Columellae 18-50 μm in diameter, hemispherical to subglobose, smooth, often collapsing, without adhering sporangia remnants. Sporangiospores 5-8×2.5-5 μm, subglobose to irregularly elliptical, or angular in sideview, with faint to prominent longitudinal striations, hyaline to pale yellowish brown.

Although the invention is discussed hereinbelow principally with respect to a specific strain, not only the strain described above, but varieties and mutants, whether obtained by natural selection, produced by the action of various mutating agents such as ionizing radiation or chemical agents such as nitrosoguanidine are contemplated within the scope of the present invention.

Compound IA may be produced by cultivating *Rhizopus arrhizus* ATCC 11145 in a suitable nutrient medium containing Compound Z under conditions hereinafter described and thereafter recovering from the product medium by extracting the desired product from the fermentation medium with a suitable solvent, concentrating the component containing the desired compound, and then subjecting the concentrated material to chromatographic separation.

The cultivation is carried out in a medium containing sources of carbon and nitrogen assimilable by the microorganism.

The sources of carbon include glycerol, sugars, sugar alcohols, starches and other carbohydrates, or carbohydrate deivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 40 percent by weight of the medium is satisfactory. These carbon sources can be used individually or several such carbon sources may be combined in the same medium.

The sources of nitrogen include amino acids such as glycine, arginine, threonine, methionine and the like, ammonium salt, and complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 10 per cent by weight of the medium.

In addition, the medium should contain a phosphate salt. The phosphate salt should be at least about 10 percent by weight of the solid components. It is preferably from about 12 to about 15 percent. A particularly suitable medium is soy-glucose medium of the following composition which may be employed both as a seed medium and a culture medium:

| Soy-Glucose Medium | g/l |
|---|---|
| Glucose | 20.0 |
| Soya meal | 5.0 |
| Fidco yeast extract* | 5.0 |
| NaCl | 5.0 |
| $K_2HPO_4$ | 5.0 |
| Adjust pH to 5 | |

*Fidco yeast extract is a nitrogen source, product of Difco Laboratories, Detroit MI.

The fermentation may be carried out by first preparing a seed culture. In preparing a seed culture, spores of *Rhizopus arrhizus* are obtained from oatmeal agar slants of MF 4974 maintained in the Merck Culture Collection and dispersed in water to obtain a spore suspension containing about $7\times10^9$ spores per milliliter.

The spore suspension of MF 4974 is inoculated into a seed flask containing the soy glucose broth and the inoculated suspension incubated on a rotary shaker in the temperature range of from about 15° C. to about 30° C., preferably 25° to 28° C. The agitation may be up to 400 rpm but generally about 220 rpm is preferred. The incubation is carried out over a period of at least 24 hours to about two days.

When growth is abundant, the mycelia are harvested by filtering through a nylon mesh. For biophosphorylation, the mycelia are suspended in a phosphate buffer containing 3 percent glycerol or some other simple carbon source. Compound Z then is added at a concentration of about 50 μg/ml in dimethylsulfoxide (DMSO). The pH of the production medium is important. The flasks are incubated, preferably with shaking at 220 rpm at 27° C. for 24 to 48 hours to produce Compound IA. It is critical that it be maintained in the range of about 6.0 to 6.3.

After completion of the incubation period the contents of all the flasks are pooled and filtered through a nylon mesh filter. The mycelial cake on the filter is slurried with aqueous methanol and filtered. The procedure is repeated with the filter cake and the filtrate loaded onto a styrene/divinylbenzene column. The column is then washed with water and the phosphorylated product eluted with 20 percent aqueous acetonitrile and the remaining metabolite and substrate eluted with 70 percent aqueous acetonitrile.

After elution, the fractions may be assayed by HPLC. The fractions determined to have the desired product as indicated by a retention time of 12.8 minutes are combined and concentrated under reduced pressure to obtain the product as residue.

The salts, i.e., where R is a cationic salt of the phosphate, may be prepared by intimately contacting a base corresponding to the cation in an alcoholic or other polar solvent, then concentrating to initiate crystallization of the salt. Thereafter, the salt is recovered by filtration.

One method of preparing salts is to apply an aqueous solution of the acid onto a non-functionalized resin column. Representative columns include AMBERCHROM-161 (divinylbenzene/polystyrene resin, obtainable from TosoHaas, trademark name registered by Rohm & Haas) "DIAION" HP-20 and SP-207 styrene divinylbenzene and brominated styrene divinylbenzene resin respectively (products of Mitsubishi Chemical). The column is then washed with aqueous $MH_2PO_4$ or $M'(H_2PO_4)_2$ where M and M' are monovalent and divalent cations respectively, thereby converting the acid to a mono-cation salt form. The column is washed with water to remove excess inorganic phosphate salt. The product M or M' salt is then removed from the column by applying an aqueous eluant having greater than 50 percent organic content. Useful eluants are 80 percent acetonitrile, 80 percent ethanol or 80 percent methanol. The product is isolated by concentration to dryness and/or lyophilization of the eluate.

This procedure also may be employed to prepare one salt from another.

Alternatively, the acid is dissolved in an aqueous mobile phase containing low amount of organic solvent such as acetonitrile and containing phosphate salt thereby forming a solution of the salt of the acid. The solution is subjected to reduced pressure to remove the acetonitrile, then applied to a C-18 extraction column to retain the salt of the product on the column. The salt of the product then may be removed as above described.

As previously noted, the phosphate is a compound which is active against certain yeast fungi such as *C. albicans* and *C. tropicalis*. The activity may be seen in a microbroth dilution assay employing a Yeast Nitrogen Base (Difco) with 1% dextrose (YNBD). In carrying out the assay, Compound IA was solubilized in 10 percent dimethyl sulfoxide (DMSO) and diluted to 2560 μg/ml. The compounds were further diluted to 256 μg/ml in YNBD. Then 0.15 ml of the suspension was dispensed to the first row of a 96-well plate (each well containing 0.15 ml of YNDB) resulting in a drug concentration of 128 μg/ml. Two-fold dilutions were then made to obtain final drug concentrations ranging from 128 to 0.06 μg/ml.

The yeast cultures, maintained on Sabouraud dextrose agar were transferred to YM broth (Difco) and incubated overnight at 35° C. with shaking (250 rpm). After incubation, each culture was diluted in sterile water to yield a final concentration of $1-5\times10^6$ colony forming units (CFU)/ml.

96-well microplates were inoculated using a MIC-2000 (Dynatech) which delivers 1.5 μl per well yielding a final inoculum per well of $1.5-7.5\times10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 μl samples from the wells in the 96-well microplate were transferred to a single well tray containing Sabouraud dextrose agar. The inoculated trays were incubated 24 hours at 28° C. and then read. The MFC is defined as the lowest concentration of drug showing no growth or less than 4 colonies per spot.

| Fungus Strain No. | Minimum Fungicidal Concentration (μg/ml) Compound IA |
|---|---|
| *Candida albicans* | |
| MY 1055 | 64 |
| MY 1028 | 64 |
| *Candida tropicalis* | |
| MY 1012 | 32 |

The foregoing illustrates particular suitability for treating mycotic infections.

The compounds of the present invention may be employed in inhibiting or alleviating *Pneumocystis carinii* infections. In such use, Compound I or a composition containing Compound I may be administered in a therapeutically effective or inhibitory amount to subjects infected with or susceptible to being infected with *Pneumocystis carinii*.

The suitability of the compounds of the present invention for therapeutic or anti-infective purposes may be determined in studies on immunosuppressed rats when Sprague-Dawley rats (weighing approximately 200 grams) are immunosuppressed with dexasone in the drinking water (2.0 mg/L) and maintained on a low protein diet for five weeks to induce the development of pneumocystis pneumonia from a latent infection. Before drug treatment, two rats are sacrificed to confirm the presence of *Pneumocystis carinii* pneumonia (PCP). Six rats then are injected twice daily for four days intravenously (I.V.) via the tail vein with Compound I in 0.25 ml of vehicle (distilled water). A vehicle control is also carried out. All animals continue to receive dexasone in the drinking water and low protein diet during the treatment period. At the completion of the treatment, all animals are sacrificed, the lungs are removed and processed, and the extent of disease determined by microscopic analysis of stained slides.

A similar experiment may be carried out in which the rats are injected intraperitoneally (I.P.) twice daily for four days and then sacrificed, the lungs removed and processed, and the extent of disease determined by microscopic analysis of stained slides.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound I. Concentrate compositions suitable for dilutions prior to use may contain 90% or more by weight. The compositions include compositions suitable for rectal, topical, parenteral (including subcutaneous, intramuscular, and intravenous), pulmonary (nasal or buccal inhalation), nasal administration, or insufflation. The compositions may be prepacked by intimately mixing Compound I with the components suitable for the medium desired.

When the compound is for antifungal use any method of administration may be used. For treating mycotic infection, oral administration is frequently preferred. When oral administration is to be employed, it may be with a liquid composition or a solid composition. For liquid preparations, the therapeutic agent is preferably formulated with water or aqueous compositions, but if desired, may be formulated with glycols, oils, alcohols, and the like. For solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Composition in unit dosage form constitutes an aspect of the present invention.

The Compound I is preferably formulated in aqueous therapeutic compositions for intravenous or intraperitoneal injection or aerosol when use against *Pneumocystis carinii* is contemplated, and may be presented in unit dosage form in ampoules or in multidose containers, if necessary with an added preservative. The compositions may also take such forms as solutions in aqueous vehicles such as 0.85 percent sodium chloride or 5 percent dextrose in water, and may contain formulating agents such as stabilizing and/or dispersing agents. Buffering agents as well as additives such as saline or glucose may be added to make the solutions isotonic. The drug also may be solubilized in alcohol/propylene glycol or polyethylene glycol for drip intravenous administration. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention may contain from 100 to 1000 milligrams of one of the compounds.

When the compound is to be employed for control of pneumocystis infections it is especially desirable to directly treat lung and bronchi. For this reason, inhalation methods are preferred. For administration by inhalation, the compounds of the present invention are conveniently delivered in the form of an aerosol spray presentation from pressurized packs of nebulisers. The preferred delivery system for inhalation is a metered dose inhalation (MDI) aerosol, which may be formulated as a solution of Compound I in suitable propellants, such as fluorocarbons or hydrocarbons.

Although the compounds of the present invention may be employed as tablets, capsules, topical compositions, insufflation powders, suppositories and the like, the advantage of the derivatives of the present invention over the parent lipopeptide is in their water solubility. Hence, the compounds of the present invention are most effectively utilized in injectible formulations and also in liquid compositions suitable for aerosol sprays.

The following examples illustrate the invention but are not to be construed as limiting:

EXAMPLE I

A culture of *Rhizopus arrhizus* MF 4974 from the Merck Culture collection was inoculated in 50 milliliters of soy-glucose medium in a 250 milliliter flask and the flask incubated on a rotary shaker at 220 rpm at 27° C. for 24 hours to obtain the first stage seed culture. 2.5 milliliters of this seed culture was inoculated into each of 18 flasks containing 50 milliliters of soy-glucose medium which was also charged with Compound Z to a concentration of 5 μg/ml in 50 microliters of DMSO and the resulting culture incubated on a rotary shaker at 220 rpm at 27° C. for 18 hours.

Following incubation, each flask was harvested by centrifugation, the mycelium washed twice with sterile saline and resuspended in pH 7.0 phosphate buffer containing 1 percent glycerol. Compound Z was added to a final concentration of 58 μg/ml using 100 μl of (DMSO). The flasks were incubated on a rotary shaker at 220 rpm at 27° C. for 48 hours.

At the end of this period, the contents of eighteen flasks (900 milliliters) were pooled and the whole broth centrifuged. The mycelial cake was slurried with 100 milliliters of water, the pH adjusted to 3.5 and the slurry extracted twice with 100 milliliters of n-butanol. The supernatant was acidified to pH 3.5 and extracted twice with one-half the volume of n-butanol. Each organic extract was assayed by HPLC. The assay condition was as follows:

Column: "ZORBAX" (DuPont) C8 Rx 4.5×250 mm
Mobile Phase: Acetonitrile+10 mM aq. $KH_2PO_4$, gradient 20% to 80% over 20 minutes
Temperature: 45° C.
Flow rate: 1.5 ml/min.
Detection: 210 nm Sample Vol: 50 μl The extracts of the mycelium and the extracts of the supernatant were pooled and evaporated to dryness at 30° C. at reduced pressure to obtain an oil as residue.

The oil was dissolved in the mobile phase of 40/60 acetonitrile/water and further purified using "ZORBAX" C8 (9.6 mm×25 cm) semi-preparative column. The column was developed at 7.05 ml/min. using 40 percent aqueous acetonitrile containing 0.1 percent trifluoroacetic acid (TFA) at 45° C. Fractions having a retention time of 12.8 minutes were pooled, and the solvent evaporated to obtain 12 mg of Compound IA in a yield which calculated to be 24%.

The product had the mass spectral data previously set forth.

A portion of the product was converted to the monopotassium salt. This was carried out by dissolving the biophosphorylation product in 70 percent aqueous acetonitrile containing 10 mM $KH_2PO_4$ (pH 4.5). The mixture was subjected to reduced pressure to remove the acetonitrile and the aqueous residue loaded onto a water-equilibrated C-18 solid phase extraction column. The column was washed with water and then eluted with 70 percent aqueous acetonitrile and the eluate freeze-dried for retention of the salt.

EXAMPLE II

Spores of *Rhizopus arrhizus* were obtained from oatmeal agar slants of MF 4974 maintained in the Merck Culture Collection and employed to prepare a spore suspension in water of about $7\times10^9$ spores per milliliter for use in the preparation of seed culture.

Seed flasks each containing 500 milliliters of soy glucose broth of the composition previously given, were inoculated with 1 milliliter of spore suspension and incubated on a rotary shaker (220 rpm) at 27° C. for 24 hours.

Following incubation, the mycelia from each flask were harvested by filtering through a 10 micron nylon mesh and then resuspended in an equal volume of a 100 mM pH 6.3 phosphate buffer containing 3 percent glycerol and added to the broth. Compound Z, was added to a concentration of about 50 μg/ml in dimethylsulfoxide. The flasks were then incubated on a rotary shaker at 220 rpm at 27° C. for 24 hours.

After completion of the incubation period, the contents of sixteen flasks totaling 8000 milliliters were pooled and filtered through a 10 micron nylon mesh. The mycelial cake was slurried with 1000 milliliters of 50 percent aqueous methanol and filtered. The mycelial cake was again extracted with aqueous methanol and the two aqueous methanol filtrates combined and diluted with 2000 milliliters of water.

The resulting aqueous solution was applied to a 15 mm×300 mm column packed to a 220 mm bed height with water equilibrated "DIAION" HP20 resin. The filtrate was pumped in a downflow mode at 15 ml/min. in 2000 ml aliquots. After loading, the column was washed with 500 milliliters of water and the desired phosphorylated product eluted with 500 milliliters of 20 percent aqueous acetonitrile. The remaining substrate and metabolite was eluted with 500 milliliters of 70 percent aqueous acetonitrile.

The diluted filtrates from the mycelial extracts were also pumped onto the column, the column washed and then eluted and the eluate assayed by HPLC. The assay condition was as described in Example I.

HPLC indicated the following mass balance for microbial phosphorylation and "DIAION" HP 20 isolation:

Substrate Charged: 402.5 mg
Metabolite and Substrate Recovered: 383.8 mg
Total Recovery: 95.4%
Compound IA 234.9 mg
Bioconversion yield: 61.2%

The eluate was concentrated under reduced pressure and the residue dissolved in 40 percent aqueous acetonitrile containing 10 mM $KH_2PO_4$ to obtain a monopotassium salt. The aqueous solution was subjected to reduced pressure to remove the acetonitrile and the aqueous residue loaded onto a water-equilibrated C-18 solid phase extraction column. The column was thereafter washed with water and then the monopotassium salt of Compound I eluted with 70 percent aqueous acetonitrile. The eluant was freeze dried to obtain the salt. The NMR spectrum of this salt is that previously detailed.

The salt is converted to the acid by careful acidification.

EXAMPLE III

The following salts are prepared by reacting an appropriate phosphate salt and Compound I in the manner described in Example II and concentrating under vacuum.

| Example No. | R |
|---|---|
| IIIa | PO(OH)(ONa) |
| IIIb | PO(OH)(OK) |
| IIIc | $PO(ONa)_2$ |
| IIId | PO(OLi)(OH) |
| IIIe | $PO(OH)(OMg)_{\frac{1}{2}}$ |
| IIIf | $PO(OH)(ON(CH_3)_4)$ |

EXAMPLE IV 1000 compressed tablets each containing 500 mg of Compound IA are prepared from the following formulation:

| Compound | Grams |
|---|---|
| Compound IA | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE V 1000 hard gelatin capsules, each containing 500 mg of mono sodium salt of Compound I are prepared from the following formulation:

| Compound | Grams |
|---|---|
| Compound I, mono sodium salt | 500 |
| Starch | 750 |
| Dibasic calcium phosphate hydrous | 5000 |
| Calcium stearate | 2.5 |

A uniform mixture of the ingredients is prepared by blending and used to fill two-piece hard gelatin capsules.

250 ml of an injectable solution are prepared by conventional procedures having the following formulation:

| | |
|---|---|
| Dextrose | 12.5 g |
| Water | 250 mL |
| Compound I, mono potassium salt | 400 mg |

The ingredients are blended and thereafter sterilized for use.

EXAMPLE VI

An aerosol composition may be prepared having the following formulation:

| | Per Canister |
|---|---|
| Compound IA | 24 mg |
| Lecithin NF Liquid Concentrated | 1.2 mg |
| Trichlorofluoromethane, NF | 4.026 g |
| Dichlorodifluoromethane, NF | 12.15 g |

Preparation of Starting Materials

Compound Z, the starting material, was prepared by inoculating 54 milliliters of P34-2 medium of the following composition per liter: corn steep liquor, 5 g; D-mannitol 25 g; glucose monohydrate, 10 g; "PHARMAMEDIA," (nonhydrolyzed protein, Buckeye Oilseed Products, Memphis, Tenn.) 20 g $KH_2PO_4$, 9 g; $FeSO_4.7H_2O$, 10 mg $MnSO_4.4H_2O$ 10 mg; $CuCl_2.2H_2O$, 0.25 mg; $CaCl_2.2H_2O$, 1 mg; $H_3BO_3$, 0.56 mg: $(NH_4)_6$ $Mo_7O_{24}$.-$H_2O$, 0.19 mg; $ZnSO_4.7H_2O$, 2 mg, with frozen vials of *Zalerion arboricola* MF5533 ATCC 74030 and the inoculated medium incubated with shaking at 220 rpm at 25° C. for four days. Twenty milliliters were used to inoculate four 2-liter flasks containing 500 milliliters of P34-2 medium and the inoculated medium incubated at 25° C. for four days at 220 rpm. The flask contents were pooled and used to inoculate into three fermenters each containing 180 liters of P34-2 medium and 2 ml/L of propylene glycol P-2000 (Dow Chemical) to reduce foaming and the inoculated medium cultivated for six days at 25° C., an air flow of 90 L/min. a pressure of 0.7 kg/cm$^2$ gauge, and an agitator speed of 200 rpm. A 25 liter sample of the resulting broth was then used to inoculate three fermenters each containing 475 liters of P34-2 medium containing 2 ml/L of P-2000 and cultivated for four days at 25° C., air flow of 250 L/min, pressure 0.7 kg/cm$^2$ gauge and 150 rpm.

425 liters of this seed broth was inoculated into each of three production fermenters containing 13,700 liters of TG106 medium of the following composition per liter: D-mannitol, 100 g; NZ-Amine type E (casein hydrolysate, Sheffield Products, Kraft Inc.) 33 g; Fidco 8005 yeast extract (Difco), 10 g; $(NH_4)_2SO_4$, 5 g; $KH_2PO_4$, 9 g; P-2000, 2 ml, and the fermenters operated at a temperature of 27° C., air flow of 2500 liters/minute, a pressure of 0.7 kg/cm$^2$ gauge, and an agitator speed of 50 rpm. The pH was allowed to decrease from 6.0 to 5.5 and then maintained at 5.5±3. After about 2½ weeks the broth was harvested for product isolation.

The broth from the foregoing cultivation was first extracted with an equal volume of methanol. The methanol-broth was clarified using a liquid-solid separator (centrifuge) to obtain clarified liquid as first extract and solid. The extraction-clarification was repeated. The extracts were combined and the water content adjusted to about 50 percent. The resulting solution was passed through a "DIAION" SP-207 adsorption column to adsorb Compound Z and the column washed with aqueous methanol. Thereafter Compound Z was recovered with 100 percent methanol.

The water content of the methanol containing Compound Z was adjusted to 50 percent and the aqueous methanol solution intimately mixed with an equal volume of 1:1 ethyl acetate/hexane and the two liquid phases thereafter separated. The aqueous methanol layer was passed through a column of "DIAION" SP-207, the column washed with aqueous methanol, and Compound Z eluted with 100 percent methanol. The eluant was vacuum concentrated to a minimum volume and the solvent composition adjusted to about 75:20:5 ethyl acetate/methanol/water.

The feed thus prepared was passed through a silica gel column and Compound Z eluted with 85:10:5 ethyl acetate/methanol/water. The fractions showing 85 percent or greater area purity by HPLC were combined, vacuum concentrated to remove ethyl acetate and the concentrate adjusted to 50 percent aqueous methanol, the latter passed through "DIAION" HP-20 in the manner previously described concentrated and Compound Z precipitated with acetronitrile and recovered by vacuum filtration and then dried.

The starting material also may be prepared by methods described in copending applications Ser. Nos. 47/492,025 and 47/492,026.

*Z. arboricola* MF5533 ATCC 74030 is disclosed and claimed in copending application Ser. No. 630,457, filed Dec. 19, 1990 still pending. Briefly, it may be obtained by (a) inoculating a frozen vegatative mycelium of *Z. arboricola* ATCC 20957 (disclosed and claimed in copending application Ser. No. 492,024 filed Mar. 12, 1990, now abandoned) into KF seed medium of: corn steep liquor, 5 g/l; tomato; tomato paste 40 g/l, oat flour 10 g/l; glucose 10 g/l; $FeSO_4.7H_2O$ 10 mg/l; $MnSO_4.4H_2O$ 10 mg/l; $CuCl_2.2H_2O$, 0.25 mg/l; $CaCl_2.2H_2O$, 1 mg/l; $H_3BO_3$, 0.56 mg/l; $(NH_4)_6Mo_7O_{24}.H_2O$, 0.19 mg/l; $ZNSO_4.7H_2O$, 2 mg/l; adding to the medium N-methyl-N'-nitro-N-nitrosoguanidine (NTG) (b) cultivating, thereafter (c) plating a portion of the growth on potato dextrose agar and (d) incubating for 14 days at 25° C. to obtain spores then (e) harvesting the spores, (f) diluting the spores with sterile saline (g) plating on potato dextrose agar (h) incubating for 7 days for colony formation, (i) transferring separate colonies to slants of potato and (j) incubating for 14 days at 25° C.

SEQUENCE LISTING ( 1 ) GENERAL INFORMATION:

( i i i ) NUMBER OF SEQUENCES: 1

-continued ( 2 ) INFORMATION FOR SEQ ID NO: 1:

( i ) SEQUENCE CHARACTERISTICS:

( A ) LENGTH: 6
( B ) TYPE: AMINO ACID
( C ) STRANDEDNESS: NA
( D ) TOPOLOGY: CIRCULAR ( i i ) MOLECULE TYPE:

( A ) DESCRIPTION: PEPTIDE ( i i i ) HYPOTHETICAL: NO
( i v ) ANTI-SENSE:
( v ) FRAGMENT TYPE: NOT KNOWN
( v i ) ORIGINAL SOURCE:
( v i i ) IMMEDIATE SOURCE:
( v i i i ) POSITION IN GENOME:
( i x ) FEATURE:
( x ) PUBLICATION INFORMATION:
( x i ) SEQUENCE DESCRIPTION: SEQ ID NO: 1:

Xaa Thr Xaa Xaa Xaa Xaa
1 5

What is claimed is:

1. A phosphorylated cyclic lipopeptide compound having the formula SEQ ID NO: 1:

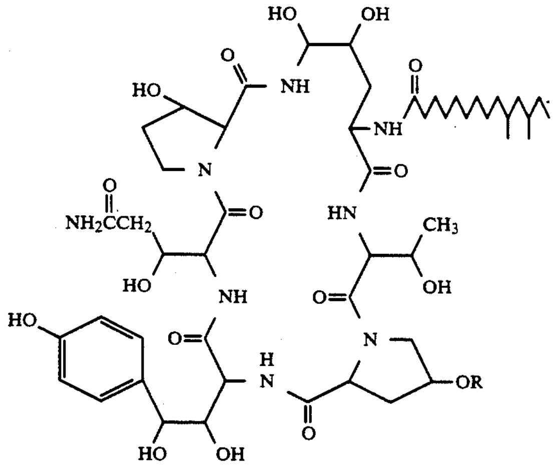

wherein R is

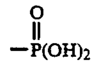

or a cation salt thereof.

2. A compound according to claim 1 wherein R is

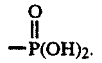

3. A compound according to claim 1 wherein R is

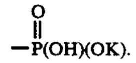

4. A compound according to claim 1 wherein R is

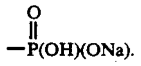

5. An antifungal composition comprising an effective amount of a compound of claim 1 in admixture with a pharmaceutically acceptable carrier.

6. A method for controlling the growth of fungi comprising administering an antifungally effective amount of the compound of claim 1.

* * * * *